United States Patent [19]

Kelman

[11] 4,092,743

[45] June 6, 1978

[54] INTRAOCULAR LENSES

[76] Inventor: Charles D. Kelman, 73 Bacon Rd., Old Westbury, N.Y. 12123

[21] Appl. No.: 791,693

[22] Filed: Apr. 28, 1977

Related U.S. Application Data

[63] Continuation-in-part of Ser. No. 728,973, Oct. 4, 1976, abandoned.

[51] Int. Cl.² ............................ A61F 1/16; A61F 1/24
[52] U.S. Cl. ......................................................... 3/13
[58] Field of Search ........................................... 3/13, 1

[56] References Cited

U.S. PATENT DOCUMENTS

| 3,458,870 | 8/1969 | Stone | 3/13 |
| 3,979,780 | 9/1976 | Boniuk | 3/13 |

OTHER PUBLICATIONS

"Experience with Twelve Cases of Intra-Ocular Anterior Chamber Implants for Aphakia", by J. Boberg--ANS, British Journal of Ophthalmology, vol. 45, No. 1, Jan. 1961, pp. 37–43, 3–13.

"The Mark VI, Mark VII and Mark VIII Choyce Anterior Chamber Implants", Proceedings of The Royal Society of Medicine, vol. 58, Sep. 1965, pp. 729–731, 3–13.

*Primary Examiner*—Ronald L. Frinks

*Attorney, Agent, or Firm*—Henry Sternberg

[57] ABSTRACT

A new intraocular lens construction, suitable for use in artifical lens implantations and having a medial light-focusing lens body and two lateral position fixation elements therefor, is disclosed. One of the position fixation elements has a first portion extending generally laterally from a first region of the periphery of the lens body, and a second portion extending from the first portion generally transversely thereto and at least partly peripherally of the lens body. The other position fixation element extends generally laterally from a second region of the periphery of the lens body spaced from the first region. By virtue of the special construction of the first position fixation element, the lens can be introduced into the eye by being in effect snaked through the corneo-scleral incision. The length of the incision thus can be the minimum required, as a function of the diameter of the lens body for a given thickness thereof, to accommodate the lens body and can be considerably less than is required in cases of lens implantations utilizing currently available intraocular lenses. By virtue of the location and orientation of the transverse second portion of the first position fixation element relative to the second position fixation element, the two elements coact to provide a three-point support for the lens in the eye so as to maintain proper lens positioning relative to the pupil of the eye.

26 Claims, 11 Drawing Figures

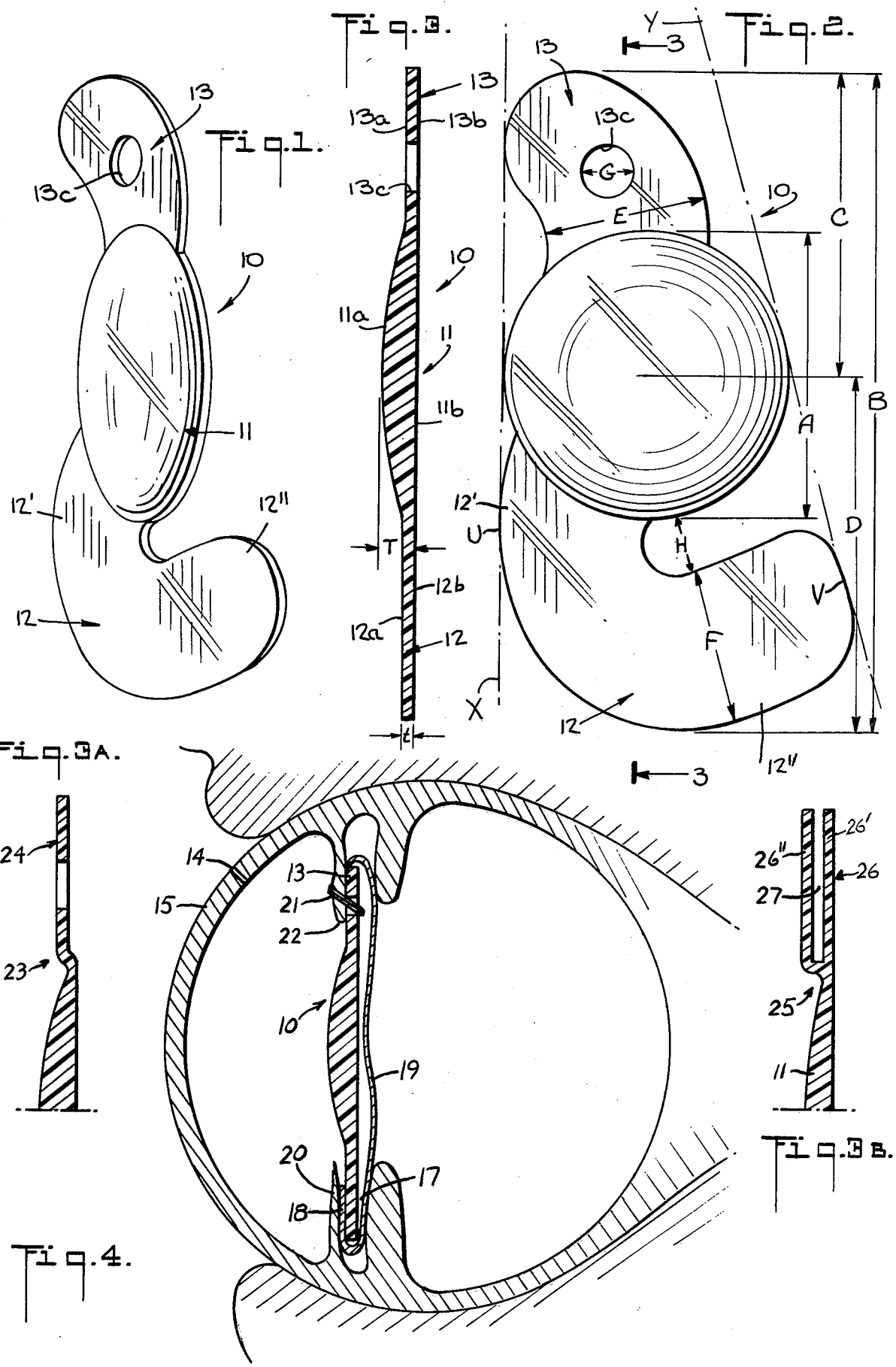

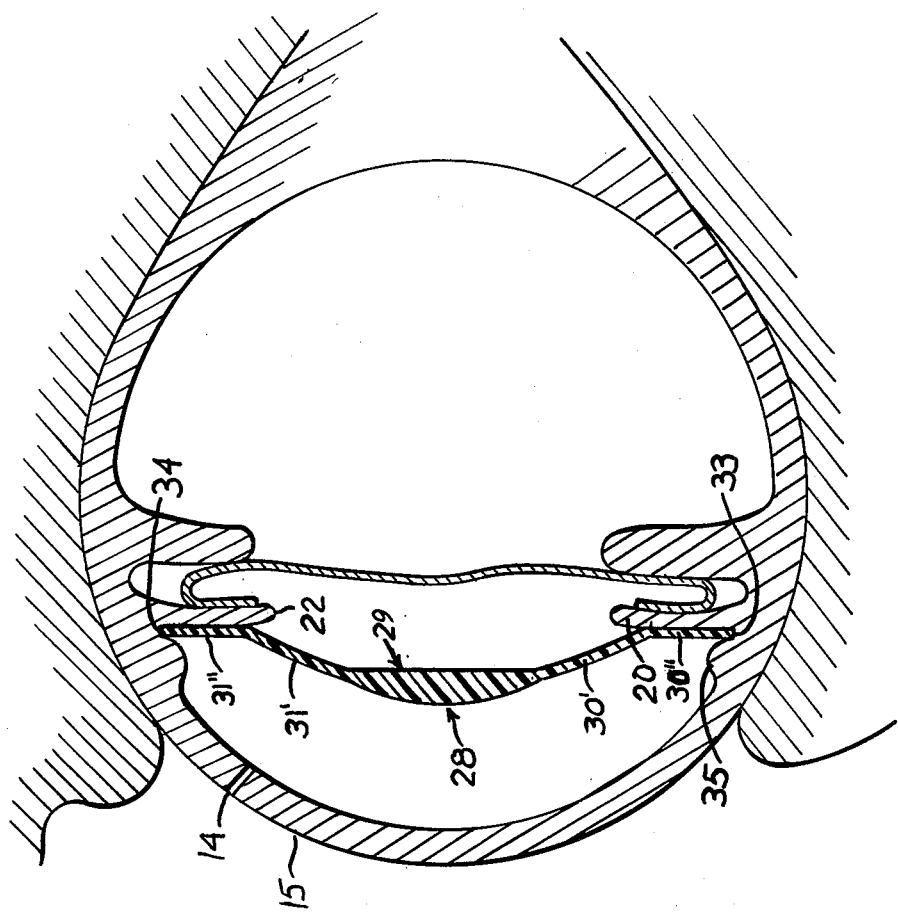
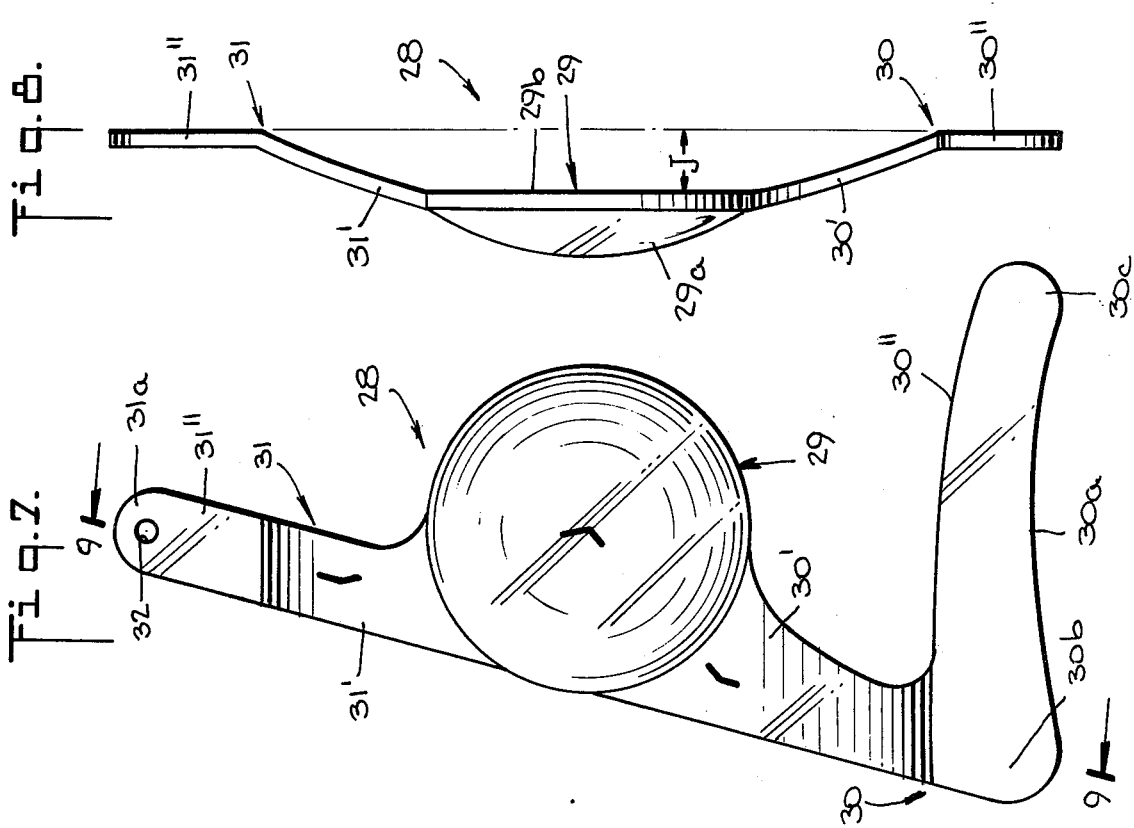

INTRAOCULAR LENSES

This application is a continuation-in-part of my prior application Ser. No. 728,973, filed Oct. 4, 1976 and now abandoned.

This invention relates to intraocular lenses suitable for use as artificial lens implants.

Lens implantation is a surgical technique which in recent years, based to a large extent on the work and experiences of Drs. C. D. Binkhorst and J. G. F. Worst in Holland, has come into increasing use for the correction of aphakia resulting from the surgical extraction (either extracapsular or intracapsular) of the natural lens from the patient's eye because of a blindness-causing condition such as cataract. In general format, an intraocular lens consists of a medial lens body about 4 mm in diameter and a plurality of lateral lobes usually projecting from different sides of the lens body for use in fixing the lens in position in the eye. Within the basic format, however, several different designs of intraocular lenses are currently available. In most of these, the lobes or position fixation elements are in the form of two or more metallic loops, with each loop being constituted by a short length of wire of a metal such as platinum-iridium, and with each wire being anchored at its two ends on the posterior surface of the lens body. In some lenses, anteriorly as well as posteriorly mounted loops are provided. Each such loop extends generally radially of the lens body, and the various loops are spaced from one another peripherally of the lens body and are disposed in a common plane spaced from the posterior surface of the lens body (or the anterior surface in the case of anterior loops). Another type of intraocular lens which has recently been developed utilizes four lobes or position fixation elements which are integral parts of the lens and arranged in a "maltese cross" configuration about the lens body. In this type of lens, the lobes are disposed in generally the same plane as the lens body.

As is well-known to those skilled in this art, even though the diameter of the lens body of an intraocular lens is only about 4 mm, for the purpose of a lens implantation, a corneo-scleral incision considerably longer than the lens body diameter, and normally from about 8 to 9 mm in length, is required. An incision of this magnitude is mandated because the incision must be capable of being spread far enough to accommodate both the thickness and the width of the lens. In this context, "thickness" means the dimension of the lens as measured from the anteriormost plane in which any part of the lens structure (e.g. the apex of the lens body) is found, to the posterior-most plane (e.g. the plane of the position fixation elements). "Width" means the minimum length of a projection of the lens onto a plane parallel to the optical axis of the lens body, in a direction perpendicular to a projection of the optical axis on such plane, which can be achieved by rotating the lens 360° about said optical axis.

Lens implantations are not only extremely difficult and delicate operations, but the use of the currently available intraocular lenses, even by a highly skilled surgeon, entails a number of disadvantages. One of these is that a relatively long incision, generally double the diameter of the lens body or more, is required because of the mechanical, i.e. lens dimension, aspects mentioned earlier. The problem which ensues here is, of course, that the longer the incision, the greater the wound and the more difficult the post-operative recovery and healing period for the patient. Another disadvantage is that lenses are somewhat difficult to manipulate, given the relatively cramped environment of the surgical operation involved. An improper fixation of the lens relative to the pupil thus can easily occur, which will make it necessary for the surgeon, despite the possible traumatic effects on the patient, to go back into the eye within a few days after the initial surgery in order to correct the positioning error.

It is an important object of the present invention, therefore, to provide a class of novel and highly improved intraocular lenses which will both substantially simplify lens implantation surgery and enable the aforesaid disadvantages to be minimized if not avoided altogether.

A more particular object of the present invention is the provision of intraocular lenses so constructed that they will be easier to insert properly in position than heretofore known lenses and that they will enable use of a corneo-scleral incision of considerably less length than has heretofore been required in implanting the known lenses.

Basically speaking, the objectives of the present invention are achieved by an intraocular lens construction which is characterized by a medial lens body and only two position fixation elements projecting from spaced, generally opposite lateral regions of the lens body. One of these elements has a first portion extending generally laterally from the lens body and a second portion extending from the end of the first portion generally transversely thereto and at least partly peripherally of the lens body, while the other element extends generally laterally from the lens body. The maximum width of any portion of either position fixation element for a given thickness thereof is such that it can be accommodated in and pass through the minimum length incision which is required to accommodate and permit passage of the lens body. Preferably, both elements are unitary with the lens body, i.e. they are not separately attached elements but are formed with the lens body (by molding or machining, for example) of a single block of any suitable physiologically inert and non-toxic synthetic plastic material such as are well known to the art, e.g. polymethylmethacrylate, but the position fixation elements may, as long as they have the requisite shapes and orientations, be constituted by platinum-iridium or equivalent metal wire loops such as hereinbefore mentioned.

The first portion or leg of the first position fixation element which is contiguous to the lens body, extends (as stated above) generally laterally of the lens body, while the transverse second portion of the element extends from the leg or first portion at least partly peripherally of the lens body. The said second portion must, however, be at a spacing from the periphery of the lens body sufficient easily to accommodate the thickness of the cornea and sclera of the eye, and preferably its length will be sufficient for it to extend through an arc of between about 40° and about 60° along the periphery of the lens body, with the opposite and extremities of the second portion of the first position fixation element as viewed peripherally of the lens body being, respectively, located on two imaginary lines which are tangent to the lens body at opposite sides thereof and intersect at a point spaced from the lens body on the side thereof where the second position fixation element is located.

The lens construction can also be stated in somewhat different words: first, the configurations of the two position fixation elements and their location with respect to the lens body are such that the minimum length of a projection of the entire lens onto a plane parallel to the optical axis of the lens body in a direction perpendicular to a projection of the optical axis on that plane which can be achieved by locating the lens 360° about the optical axis, is greater than the minimum length of a projection of the lens body alone onto that plane in a direction perpendicular to a projection of the optical axis on the plane which can be achieved by rotating the lens body 360° about the optical axis; second, the difference between these lengths is sufficient that an insertion of the lens, through an incision in the eye, by a movement which is generally radial with respect to the optical axis would require the length of the incision to be greater than the minimum possible length of the incision which, as a function of the thickness and lateral dimensions of the lens body, would accommodate and permit passage of the lens body alone; and third, the maximum width of each position fixation element at any part thereof for a given thickness thereof is such that the element can be accommodated in and pass longitudinally through the said minimum length incision.

In an intraocular lens according to one embodiment of the present invention, which is particularly suited for an implantation in which the first and second position fixation elements are to be seated behind the iris in the lower and upper regions, respectively, of the cul-de-sac of the anterior and posterior capsules; the two position fixation elements are in precisely coplanar relation with one another both anteriorly and posteriorly. The two position fixation elements thus are also in substantially coplanar relation with the lens body, and the term "substantially coplanar" wherever it appears in the specification and claims in this regard should be so interpreted even though the convex anterior surface of the lens body may well extend slightly beyond the anterior surface planes of the position fixation elements. As a modification of this embodiment of the present invention, it is contemplated that the second position fixation element may be offset slightly anteriorly with respect to the first position fixation element, so that it would seat against the front or anterior surface of the iris rather than behind it. As a still further modification of this embodiment of the present invention, it is contemplated that the second position fixation element may be a combination of the foregoing, i.e. it would be composed of two parallel, spaced members one of which would be in the same plane as the first position fixation element while the other would be slightly offset anteriorly relative thereto, leaving therebetween a narrow space of at most about 1 mm in width into which the iris could be fitted so as to provide a means for immobilizing the tab-like position fixation element relative to the iris that would not require suturing. In both of the two just-described modifications, however, the respective second position fixation elements are deemed to be in substantially coplanar relation with the lens body, and the term "substantially coplanar" wherever it appears in the specification and claims in this regard is to be interpreted accordingly.

The second position fixation element, when made of plastic and located so as to seat either behind or in front of the iris in the upper region of the cul-de-sac of the anterior and posterior capsules, normally will also be provided with means for enabling it to be sutured to the iris to achieve complete immobilization. Such means will preferably consist of an aperture provided within the confines of the element, but as an alternative a pair of notches could be provided on opposite side edges of the element.

In use, when a lens according to the above embodiment of the present invention is being implanted, the surgeon will first make a corneo-scleral incision in the eye only slightly longer than the diameter of the lens body, i.e. the incision will be about 5 mm in length. In order to insert the lens into the eye, the surgeon will then introduce the lens essentially "longitudinally" into the eye, i.e. he will in effect snake the lens in through the incision, starting with the free end extremity of the transverse second portion of the first position fixation element and ending with the tip of the second element, until the lens is properly positioned in the eye. This means that the second portion of the first position fixation element is seated behind the iris in the lower region of the cul-de-sac of the anterior and posterior capsules, that the lens body is properly centered in the region of the pupil, and that the second position fixation element (sutured to the iris, if necessary) is seated behind the iris in the upper region of the capsular cul-de-sac (or in front of the iris or embracing it, as the case may be, if one or the other of the modified forms of the lens is used). It will be understood that the two position fixation elements, upon implantation of the lens, will cooperate to maintain the proper disposition of the lens body relative to the pupil of the eye.

By way of constrast to the foregoing construction, in an intraocular lens according to another embodiment of the present invention, which is particularly suited for an implantation in which the first and second position fixation elements are to be seated in front of the iris in the lower and upper regions, respectively, of the groove located behind the scleral spur, the two position fixation elements, although of respective configuration generally similar to those of the first-described embodiment, are not entirely coplanar with each other. In this lens construction, both the first portion or leg of the first position fixation element and an inner first section of the second position fixation element, while extending generally laterally from the lens body, also are inclined somewhat posteriorly of the lens body, and the transverse second position of the first fixation element and the outer or second section of the second position fixation element are generally coplanar with each other, in a plane parallel to the posterior surface plane of the lens body. It is contemplated that the degree of the said inclination of the first portion of the first position fixation element and the first section of the second position fixation element should be such that the perpendicular distance from the common posterior plane of the second portion of the first position fixation element and the second section of the second position fixation element to the posterior surface plane of the lens body is between about 0.25 and 0.75 mm and preferably about 0.5 mm. Additionally, the second or transverse portion of the first position fixation element preferably will have a slight degree of concavity, with a radius of curvature of about 180 mm, in that edge thereof which faces away from the lens body, so that at the opposite ends of the said second portion there will be defined respective downwardly directed lobes or tip regions which, upon implantation of the lens (by means of a "snaking in" procedure as previously described), will coact with the tip end region of the second section of the second position fixation element, when the same are all received in the groove behind the scleral spur, to effect an essentially three-point position fixation of the lens in the eye. The arrangement thus is such that a small gap will be maintained between the region of the anterior surface of the iris bounding the pupil and the posterior surfaces of the first portion and first section of the first and second position fixation elements, so as to avoid possible irritation of the iris in that region.

The foregoing and other objects, characteristics and advantages of the present invention will be more clearly understood from the following detailed description thereof when read in conjunction with the accompanying drawings, in which:

FIG. 1 is a perspective view of an intraocular lens according to one embodiment of the present invention;

FIG. 2 is a plan view of the lens shown in FIG. 1;

FIG. 3 is a sectional view taken along the line 3—3 in FIG. 2;

FIGS. 3A and 3B are fragmentary sectional views, similar to FIG. 3, which illustrate, respectively, two modifications of the lens according to this embodiment of the present invention;

FIG. 4 is a diagrammatic vertical section through a human eye and shows a lens according to the embodiment of FIGS. 1 to 3 implanted in the eye;

FIG. 7 is a plan view of an intraocular lens according to another embodiment of the present invention;

FIG. 8 is a side view of the lens shown in FIG. 7; and

FIG. 9 is a diagrammatic vertical section through a human eye and shows a lens according to the embodiment of FIGS. 7 and 8 implanted in the eye, the lens being shown in a section taken along the line 9—9 in FIG. 7.

Figure 5:
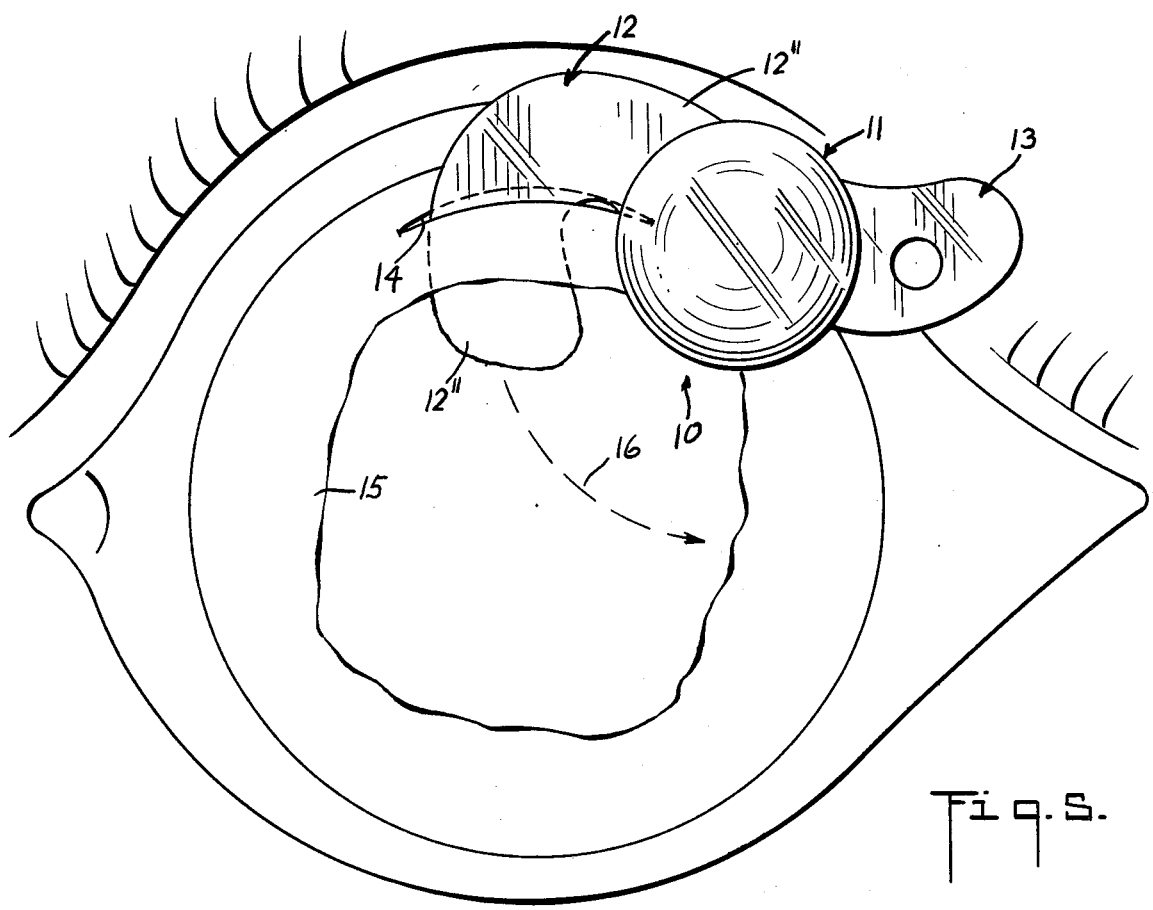
FIGS. 5 and 6 are diagrammatic front views of a human eye and, respectively, illustrate the lens positions at the start and completion of the lens implantation procedure.

Referring now to the drawings in greater detail, an intraocular lens 10 according to one embodiment of the present invention is shown in FIGS. 1 to 3. The lens 10 consists of a light-focusing lens body 11 having a convex anterior surface 11a and a flat posterior surface 11b, a first position fixation element 12 which has flat anterior and posterior surfaces 12a and 12b, and a second position fixation element 13 which has flat anterior and posterior surfaces 13a and 13b and a medial suturing aperture 13c. The thicknesses of the lens body 11 and the two position fixation elements 12 and 13 are denoted by reference characters T and t, respectively, in FIG. 3. As further clearly shown in FIG. 3, the posterior surfaces 12b and 13b of position fixation elements 12 and 13 are continuous with the posterior surface 11b of the lens body 11. Within the contemplation of the present invention, therefore, the position fixation elements are substantially coplanar with the lens body even though the convex anterior surface 11a of the latter protrudes somewhat anteriorly beyond the plane of the anterior surfaces 12a and 13a of the position fixation elements.

The position fixation element 12 includes a first or leg portion 12′ which is contiguous with and extends generally laterally from the lens body 11, and a second portion 12″, which is either imperforate as shown or may have a large opening (not shown) defined within its expanse to permit anterior and posterior capsulary adhesion to take place through the opening after implantation of the lens, and which extends generally transversely from the first portion 12″ to one side thereof along and spaced from the periphery of the lens body 11. The length of the second portion 12″ is sufficient to cover an arc of between about 40° and about 60° relative to the center of the lens body, and overall the construction is such that the oppositely lateral extremities (denoted by the reference characters U and V in FIG. 2) of the first position fixation element 12 as viewed peripherally of the lens body 11 are located on two imaginary lines, denoted by reference characters X and Y, which are tangent to the lens body at opposite sides thereof and intersect at a point (not shown because of space limitations) spaced from the lens body on the side thereof where the second position fixation element 13 is located.

The position fixation element 13 also extends generally laterally from the lens body 11 but from a region of the periphery of the latter generally opposite that where the portion 12′ of the first position fixation element 12 is located. Like the element 12, the element 13 is arcuately configured, i.e. it is devoid of sharp corners and edges, for obvious reasons. As shown in FIG. 2, the element 13 has in its outermost region a slight inclination to one side, here in a direction opposite to that of the portion 12″ of the element 12, but it should be understood that such configuration of the element 13 is not an essential characteristic and the element may instead have a slight inclination in the other direction or actually be truly straight. It is nevertheless contemplated that in case a deflection or inclination off the truly radial orientation is provided, it will not be more than about 15° to about 20°.

It will be understood, of course, that except insofar as the maximum widths of the two position fixation elements, denoted E and F in FIG. 2, must, for a given thickness $t$ thereof, be such that each element can be accommodated in and pass longitudinally through the minimum length incision which is required to accommodate the lens body because of its diameter and thickness T, the precise dimensions of the lens 10 are in and of themselves not critical aspects of the present invention, since the physiological make-up of the eyes of different human beings may well dictate the choice of lenses of slightly different dimensional characteristics. Merely by way of example, however, the following dimensions, denoted A to H in FIG. 2, might be present in a representative lens 10 according to the present invention. The lens body diameter A may be 4 mm, its maximum thickness T 0.4 mm, and the overall lens length B 9 mm, with the distance C from the center of the lens body to the end edge of the position fixation element 13 being 4 mm, and the distance D from the center of the lens body to the end edge of the position fixation element 12 being 5 mm. The maximum widths E and F of the two position fixation elements may be 2.1 mm, their thickness $t$ may be 0.2 mm, the diameter G of the suturing hole may be 0.75 mm, and the minimum width H of the space between the periphery of the lens body 11 and the proximate edge of the second portion 12″ of the first position fixation element 12 may be about 1 mm. With reference to a diametral line of the lens body parallel to the dimension line B, the arc length of the second portion 12″ of the element 12 may be 45°, and the angle between that diametral line and a line connecting the centers of the lens body and the suturing hole may be 12°. The angle of inclination of the outwardmost section of the second position fixation element 13 relative to the radial direction of the section of that element contiguous to the lens body may be 15°.

The manner of use of an intraocular lens 10 according to this embodiment of the present invention, when the same is to be implanted in the eye of a human being, will now be described with reference to FIGS. 4, 5 and 6. It is noted at this point, however, that the instant application is not intended to serve as a technically and medically complete primer for lens implantation surgery. Rather, the description and illustration of some of the surgical aspects of such an operation that are presented herein are purely diagrammatic, and they are intended only to provide basic signposts to those skilled in the art as to how such an intraocular lens is to be implanted.

Figure 6:
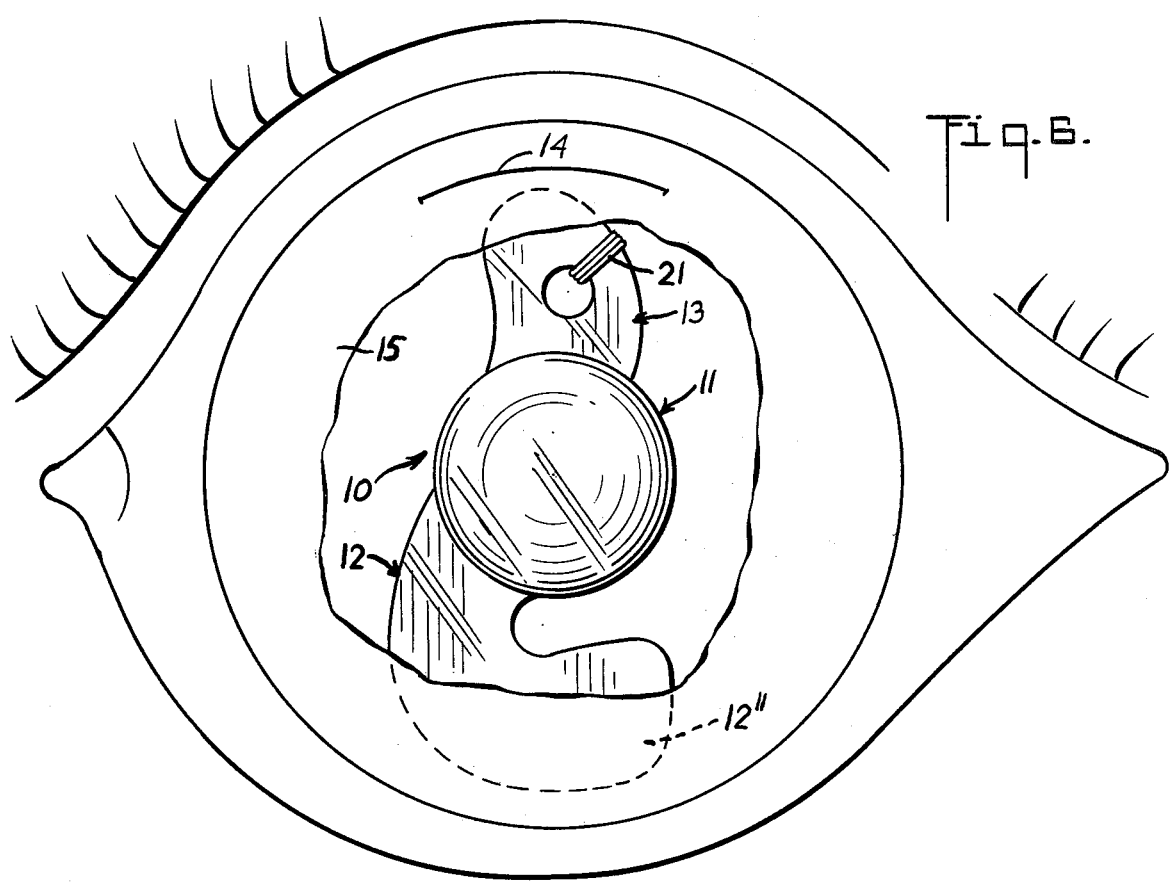

Turning now to the operation itself, assuming the patient has been properly prepared and anesthesized, the surgeon will first make a corneo-scleral incision 14 in the eyeball of the patient near the upper front region thereof, as shown in FIGS. 5 and 6. For the sake of simplicity, in those views a part of the cornea 15 is illustrated broken away, and the internal elements of the eye, such as the iris, the posterior capsules and the zonules, have been omitted entirely. The incision is made about 5 mm long, i.e. just sufficient to enable it to be spread to the degree required to accommodate both the diameter and the thickness of the lens body 11.

With the incision properly spread apart, the lens 10 is then inserted essentially "longitudinally" into the eye through the incision, i.e. starting with the free end of the second portion 12" of the first position fixation element 12 (FIG. 5). At the initial stage of the insertion, therefore, as shown in FIG. 5, the lens body 11 will be located somewhat off to one side of the incision. Once the leading end region of the portion 12" of the position fixation element 12 is disposed in the anterior chamber of the eyeball, however, the lens is in effect rotated counterclockwise, as indicated by the broken-line arrow 16, until the first portion 12' of the position fixation element 12 and the lens body 11 are located immediately in front of the incision 14. The remaining parts of the lens 10, i.e. the lens body 11 and the second position fixation element 13, are then fed through the incision. During this stage, the portion 12" of the position fixation element 12 is guided (FIGS. 4 and 6) into the lower region of the cul-de-sac 17 of the anterior and posterior capsules 18 and 19 behind the lower region of the iris 20, where the element fits in properly by virtue of its arcuate end edge, and the position fixation element 13 is inserted into the upper region of the cul-de-sac of the anterior and posterior capsules behind the upper region of the iris 20 and is sutured to the iris at that location by means of appropriate sutures 21. With the implantation so completed, the lens 10 will be securely seated in the eye, and the lens body 11 will be maintained in its proper position with respect to the pupil 22 of the eye by the cooperation of the two position fixation elements in providing a three-point fixation of the lens. Finally, of course, the incision 14 is sutured to close the wound.

In the lens according to the present invention so far described, the position fixation element 13 is adapted to seat behind the iris, as shown in FIG. 4. Should it be desired, however, to suture the position fixation element 13 to the iris at the front thereof and not to have it seated in the upper region of the cul-de-sac of the anterior and posterior capsules 18 and 19, an modified intraocular lens 23 according to the invention, as shown in FIG. 3, would be used. In the lens 23, the first position fixation element 12 (not shown in this view) is the same as shown in FIGS. 1 and 2, but the second position fixation element 24 is offset slightly, to the extent of about 1 mm, anteriorly with respect to the plane of the first position fixation element.

In accordance with the present invention also, especially if suturing of the second position fixation element to the iris is to be avoided, the immobilization of that element relative to the iris may be effected by means of a further modified lens 25 such as shown in FIG. 3B. In the lens 25, where again the first position fixation element 12 (not shown) is the same as in FIGS. 1 and 2, the second position fixation element 26 is in essence a combination of the elements 13 and 24 shown in FIGS. 3 and 3A, in that it consists of a posterior member 26' coplanar with the first position fixation element 12 and an anterior member 26" slightly offset anteriorly with respect to the member 26'. There is, accordingly, defined between the two members a narrow space 27, approximately 1 mm wide, into which the juxtaposed portion of the upper region of the iris can be inserted so as to be confined between the members 26' and 26", which would adhere to the iris sufficiently to immobilize the position fixation element 26 relative thereto. It will be apparent, of course, that the overall thickness of the position fixation element 26 in the lens 25 will be only about 1.4 mm, i.e. still less than the maximum thickness T of the lens body 11, so that there will be no interference with the passage of this position fixation element through the incision 14. As will further be clear to those skilled in the art, if desired one or both of the members 26' and 26" of the position fixation element 26 in the lens 25 may be provided with means, such as a suturing hole, to permit suturing thereof to the iris. As previously indicated, of course, the second position fixation element in any of the lens forms so far described may, in lieu of a suturing hole, be provided at its opposite side edges with a pair of appropriately arranged notches to receive the sutures.

Referring now to FIGS. 7, 8 and 9, it is also contemplated, in accordance with another embodiment of the present invention, to provide an intraocular lens 28 designed for implantation anteriorly of the iris. As shown in FIGS. 7 and 8, the lens 28 (like the lenses shown in FIGS. 1 to 6) includes a medial light-focusing lens body 29 having a convex anterior surface 29a and a flat posterior surface 29b, a first position fixation element 30 and a second position fixation element 31.

The position fixation element 30, like the element 12, has a first portion 30' extending generally laterally from one region of the periphery of the lens body 29 and a second portion 30" extending transversely from the end of the portion 30' and at least partly peripherally of the lens body. Unlike the first and second portions of the element 12, however, the portions 30' and 30" of the position fixation element 30 are not coplanar with each other or the lens body. Rather, as shown in FIG. 8, the first portion 30' is inclined somewhat posteriorly of the lens body from the region of its connection to the same, and the second portion 30" is disposed entirely posteriorly of the lens body and in a plane generally parallel to the plane of the lens body. Also, the transverse second portion 30" of the second position fixation element 30 is somewhat concavely curved on its outwardly facing edge 30a, as shown in FIG. 7, for example at a radius of curvature of about 180 mm, thereby to define at its opposite ends respective downwardly directed lobes or tip regions 30b and 30c.

Correspondingly, the second position fixation element 31, like the element 13, extends generally laterally from a second region of the periphery of the lens body spaced from and generally opposite the region where the first portion 30' of the first position fixation element 30 is located. Unlike the element 13, however, the element 31 is not coplanar with the lens body. Rather, as also shown in FIG. 8, the position fixation element 31 has a first inner section 31' which is inclined somewhat posteriorly of the lens body 29 from the region of its connection to the same, and a second outer section 31" which is disposed entirely posteriorly of the lens body and in a plane generally parallel to the plane of the lens body.

Although by virtue of the foregoing arrangement the two position fixation elements 30 and 31 are not coplanar with the lens body, the degree of inclination of the first portion 30' of the first position fixation element 30 and the degree of inclination of the first section 31' of the second position fixation element are, respectively, such as to dispose the second portion 30" of the first position fixation element and the second section 31" of the second position fixation element in coplanar relation with each other and with their posterior surfaces at a perpendicular distance J of about 0.25 to 0.75 mm from the posterior surface 29b of the lens body 29. By virtue of this arrangement, therefore, when the lens 28 has been implanted in a human eye, as shown in FIG. 9, the lens body 29 and the proximate portion 30' and section 31" of the two position fixation elements will be maintained out of contact with the iris 20 in the region of the pupil, thereby to minimize the possibility of the lens irritating the iris and interfering with the expansion and contraction of the pupil 22.

Referring again to FIG. 7, it will be seen that the second section 31" of the position fixation element 31 is provided adjacent its outer extremity with a small aperture 32, generally about 0.15 mm in diameter. In this case, however, the aperture is not a suturing hole but rather is provided only to facilitate manipulation of the lens during the insertion thereof into the eye.

It will be apparent from the foregoing that the insertion of the lens 28 through the corneo-scleral incision in the eye will be effected in the same manner, i.e. by a "snaking in" procedure, as is described hereinbefore in connection with FIGS. 5 and 6 for the lens 10, and the details of that description thus need not be repeated at this point. The ultimate position of the lens 29 will be different, however, in that the entire lens is positioned anteriorly of the iris, with the second portion 30" of the first position fixation element 30 and the second section 31" of the second position fixation element 31 seated in the lower and upper regions 33 and 34, respectively, of the groove behind the scleral spur 35. It can also be seen that by virtue of the provision of the lobes 30b and 30c on the portion 30" of the position fixation element 30, the same will coact with the lobe or tip end 31a of the second section 31" of the position fixation element 31 to provide a three-point support for the lens in the eye so as to maintain the lens body in proper position relative to the pupil of the eye.

Yet another advantage of a lens 28 according to this embodiment of the present invention is that for any given implantation operation, the selection of a lens having a vertical dimension which is precisely equal to, or in any event not greater than, the available space between the top and bottom lobe-seating regions of the groove behind the scleral spur of the patient's eye is not a matter of critical concern for the surgeon. In this context, by "vertical dimension" is meant the perpendicular distance between the plane tangent to the downwardly convex edge regions of the lobes or tips 30b and 30c of the second portion 30" of the first position fixation element 30 and a parallel plane tangent to the upwardly convex edge region of the lobe or tip 31a of the second section 31" of the second position fixation element 31. Thus, in the lens 28 the medial transverse width of the second portion 30" of the position fixation element 30 can be sufficiently reduced, for example by a suitable choice of the degree of concavity of the edge 30a, that if the surgeon happens to have used a lens which is slightly oversized by, say, a half millimeter or so with respect to the aforesaid available space in the eye, the portion 30" will be able to flex upwardly a little so as to adapt itself to the eye without placing undue stresses on, and perhaps even damaging, the tissues in the groove. The same type of upward flexure may also be accommodated by a suitable choice of the transverse width of the end region of the first portion 30' of the position fixation element 30 where that portion joins the second portion 30". If desired, of course, the contemplated upward flexure capability may be achieved by an appropriate conjoint utilization of both these approaches.

What is claimed is:

1. An intraocular lens suitable for use as an artificial lens implant,
   (A) the lens having
      (1) a medial, light-focusing lens body, and
      (2) a pair of lateral position fixation elements connected with said lens body,
   (B) one of said position fixation elements having
      (1) a first portion contiguous to and extending generally laterally outwardly from a first region of the periphery of said lens body, and
      (2) a second portion extending from said first portion generally transversely thereto and at least partly peripherally of said lens body, said second portion having that part of its peripheral edge which faces said lens body spaced from the periphery of said lens body,
   (C) and the other of said position fixation elements extending generally laterally outwardly
      (1) from a second region of the periphery of said lens body spaced from and generally opposite said first region and
      (2) in a direction generally opposite to that of said first portion of said one position fixation element,
   (D) said pair of position fixation elements cooperating to effect proper positioning and immobilization of the lens with respect to the iris of an eye of a lens implant patient,
   (E) the configurations of said position fixation elements and their location with respect to said lens body being such that
      (1) the minimum length
         (a) of a projection of the entire lens onto a plane parallel to the optical axis of said lens body in a direction perpendicular to a projection of said optical axis on such plane
         (b) which can be achieved by rotating the lens 360° about said optical axis,
      (2) is greater than the minimum length
         (a) of a projection of said lens body onto said plane in a direction perpendicular to a projection of said optical axis on such plane
         (b) which can be achieved by rotating said lens body 360° about said optical axis, (3) to an extent sufficient that insertion of the lens, through an incision in the eye, by a movement which is generally radial with respect to said optical axis would require the length of such incision to be greater than the minimum possible length of the incision which, as a function of the thickness and lateral dimensions of said lens body, would accommodate and permit passage therethrough of said lens body alone, and (F) the maximum width of each of said position fixation elements at any part thereof for a given thickness thereof being such that element can be accommodated in and pass longitudinally through said minimum length incision in the eye.

(G) whereby the entire lens is capable of being snaked into the eye of a lens implant patient through said minimum length incision.

2. An intraocular lens as claimed in claim 1, wherein said other position fixation element is provided with means to permit suturing of that element to the iris of the eye.

3. An intraocular lens as claimed in claim 2, wherein said means to permit suturing is a medial aperture provided in said other position fixation element.

4. An intraocular lens as claimed in claim 1, wherein said other position fixation element is disposed in coplanar relation with said one position fixation element.

5. An intraocular lens as claimed in claim 1, wherein said other position fixation element is offset slightly anteriorly relative to said one position fixation element.

6. An intraocular lens as claimed in claim 1, wherein said other position fixation element includes a first member coplanar with said one position fixation element and a second member parallel to said first member and offset slightly anteriorly therefrom to define a narrow space therebetween in which a juxtaposed portion of the iris can be confined.

7. An intraocular lens as claimed in claim 1, wherein the length of said second portion of said one position fixation element is such that it extends along said periphery of said lens body through an arc of between about 40° and about 60°.

8. An intraocular lens as claimed in claim 1, wherein the length of said second portion of said one position fixation element is such that it extends along said periphery of said lens body through an arc of about 45°.

9. An intraocular lens as claimed in claim 1, wherein said other position fixation element has a first portion contiguous to and oriented generally radially of said lens body, and a second portion inclined to one side of said first portion at an angle of not more than about 20° to the radial direction.

10. An intraocular lens as claimed in claim 1, wherein said position fixation elements are constructed and arranged such that said second portion of said one position fixation element and the tip end region of said other position fixation element coact to provide a three-point support for properly positioning the lens in the eye.

11. An intraocular lens as claimed in claim 10, wherein said second portion of said one position fixation element has the middle region of that part of its peripheral edge which faces away from said lens body disposed closer to said lens body than the opposite end regions of that edge, the ends of said second portion of said one position fixation element and said tip end region of said other position fixation element providing said three-point support.

12. An intraocular lens as claimed in claim 10, wherein said second portion of said one position fixation element is arcuately concave in the middle region of that part of its peripheral edge which faces away from said lens body and is arcuately convex at the opposite end regions of that edge, and said other position fixation element is arcuately convex at that part of its peripheral edge which faces away from said lens body, the convex edge regions of the ends of said second portion of said one position fixation element and the convex edge region of the tip end region of said other position fixation element providing said three-point support.

13. An intraocular lens as claimed in claim 1, (a) wherein said first portion of said one position fixation element is inclined posteriorly of said lens body from said first region of said periphery thereof, and said second portion of said one position fixation element is disposed posteriorly of said lens body and in a plane substantially parallel to the plane of said lens body, and (b) wherein said other position fixation element has a first section and a second section, said first section being contiguous with said lens body and inclined posteriorly of the same from said second region of said periphery thereof, and said second section extending from said first section and being disposed posteriorly of said lens body and in a plane substantially parallel to the plane of said lens body.

14. An intraocular lens as claimed in claim 13, wherein said second portion of said one position fixation element and said second section of said other position fixation element are disposed in substantially coplanar relation with each other.

15. An intraocular lens as claimed in claim 14, wherein said other position fixation element is provided, in said second section thereof, with a small aperture to facilitate manipulation of the lens during an implantation operation.

16. An intraocular lens as claimed in claim 14, wherein the respective inclinations of said first portion of said one position fixation element and said first section of said other position fixation element are such that the common plane of said second portion of said one position fixation element and said second section of said other position fixation element is spaced between about 0.25 mm and about 0.75 mm from said plane of said lens body.

17. An intraocular lens as claimed in claim 1, wherein the medial transverse width of said second portion of said one position fixation element is such that the free end region of said second portion can flex slightly in the direction of said lens body and said other position fixation element.

18. An intraocular lens as claimed in claim 1, wherein the transverse width of said first portion of said one position fixation element is such that said second portion of said one position fixation element can flex slightly in the direction of said lens body and said other position fixation element.

19. An intraocular lens suitable for use as an artificial lens implant,
(A) the lens having
(1) a medial, light-focusing lens body, and
(2) a pair of lateral position fixation elements connected with said lens body,
(B) one of said position fixation elements having
(1) a first portion contiguous to and extending generally laterally outwardly from a first region of the periphery of said lens body, and (2) a second portion extending from said first portion generally transversely thereto and at least partly peripherally of said lens body, said second portion having that part of its peripheral edge which faces said lens body spaced from the periphery of said lens body, (C) and the other of said position fixation elements extending generally laterally outwardly
   (1) from a second region of the periphery of said lens body spaced from and generally opposite said first region and
   (2) in a direction generally opposite to that of said first portion of said one position fixation element, (D) the oppositely lateral extremities of said one position fixation element as viewed peripherally of said lens body being, respectively, located on two imaginary lines which are substantially tangent to said lens body at opposite sides thereof and intersect at a point spaced from said lens body on the side thereof where said other position fixation element is located, and (E) the maximum width of each of said position fixation elements at any part thereof for a given thickness thereof being such that that element can be accommodated in and pass longitudinally through the minimum length incision in the eye which is required as a function of the diameter and thickness of said lens body to accommodate and permit passage of said lens body, (F) whereby the entire lens is capable of being snaked into the eye of a lens implant patient through said minimum length incision, and (G) the two position fixation elements, upon implantation of the lens, cooperate to maintain proper disposition of the lens relative to the pupil of the eye.

20. An intraocular lens as claimed in claim 19, wherein said other position fixation element is disposed in coplanar relation with said one position fixation element.

21. An intraocular lens as claimed in claim 19, wherein the length of said second portion of said one position fixation element is such that it extends along said periphery of said lens body through an arc of between about 40° and about 60°.

22. An intraocular lens as claimed in claim 19, wherein said second portion of said one position fixation element is arcuately concave in the middle region of that part of its peripheral edge which faces away from said lens body and is arcuately convex at the opposite end regions of that edge, and said other position fixation element is arcuately convex at that part of its peripheral edge which faces away from said lens body, the convex edge regions of the ends of said second portion of said one position fixation element and the convex edge region of the tip end region of said other position fixation element providing a three-point support for effecting the proper disposition of the lens in the eye.

23. An intraocular lens as claimed in claim 19, wherein the medial transverse width of said second portion of said one position fixation element is such that the free end region of said second portion can flex slightly in the direction of said lens body and said other position fixation element.

24. An intraocular lens as claimed in claim 19, wherein the transverse width of said first portion of said one position fixation element is such that said second portion of said one position fixation element can flex slightly in the direction of said lens body and said other fixation element.

25. An intraocular lens suitable for use as an artificial lens implant,
   (A) the lens having
      (1) a medial, light-focusing lens body, and
      (2) a pair of lateral position fixation elements connected with said lens body,
   (B) one of said position fixation elements having
      (1) a first portion contiguous to and extending generally laterally outwardly from a first region of the periphery of said lens body, and
      (2) a second portion extending from said first portion generally transversely thereto and at least partly peripherally of said lens body, said second portion having that part of its peripheral edge which faces said lens body spaced from the periphery of said lens body,
   (C) and the other of said position fixation elements extending generally laterally outwardly
      (1) from a second region of the periphery of said lens body spaced from and generally opposite said first region and
      (2) in a direction generally opposite to that of said first portion of said one position fixation element,
   (D) said second portion of said one position fixation element having the middle region of that part of its peripheral edge which faces away from said lens body disposed closer to said lens body than the opposite end regions of that edge, the ends of said second portion of said one position fixation element and the tip end region of said other position fixation element providing three-point support for, and cooperating to effect proper positioning and immobilization of, the lens with respect to the iris of an eye of a lens implant patient.

26. An intraocular lens as claimed in claim 25, wherein said second portion of said one position fixation element is arcuately concave in the middle region of that part of its peripheral edge which faces away from said lens body and is arcuately convex at the opposite end regions of that edge, and said other position fixation element is arcuately convex at that part of its peripheral edge which faces away from said lens body, the convex edge regions of the ends of said second portion of said one position fixation element and the convex edge region of the tip end region of said other position fixation element providing said three-point support.

* * * * *